United States Patent [19]

MacMurray

[11] 4,073,638

[45] Feb. 14, 1978

[54] WOODY STEMMED PLANT GROWTH STIMULATION

[76] Inventor: Robert R. MacMurray, 550 E. Third St., Bloomsburg, Pa. 17815

[21] Appl. No.: 679,208

[22] Filed: Apr. 22, 1976

Related U.S. Application Data

[63] Continuation-in-part of Ser. No. 526,819, Nov. 25, 1974, Pat. No. 3,967,953, which is a continuation-in-part of Ser. No. 186,508, Oct. 4, 1971, Pat. No. 3,861,801, which is a continuation-in-part of Ser. No. 815,493, April 11, 1969, Pat. No. 3,697,253.

[51] Int. Cl.$^2$ .............................................. A01N 9/20
[52] U.S. Cl. .................................... 71/100; 71/121; 71/116; 71/117
[58] Field of Search ........................................ 71/100

[56] References Cited

U.S. PATENT DOCUMENTS 3,449,111  6/1969  Wright .................................. 71/100

OTHER PUBLICATIONS

Serebrykova, Chem. Abst. vol. 77, (1972), 110531w.
Haramaki, Chem. Abst. vol. 81, (1974), 164595w.
Julliard et al., Chem. Abst. vol. 71, (1969), 11975p.
Weidman et al., Chem. Abst. vol. 77, (1972), 15470s.

Primary Examiner—Lewis Gotts
Assistant Examiner—Catherine L. Mills
Attorney, Agent, or Firm—Max R. Millman

[57] ABSTRACT

A method of stimulating the growth of woody stemmed plants by applying to the plants S-ethyl-N,N-dipropyl-thiocarbamate alone or combined with N,N-di-n-propyl-4-trifluoromethyl-2,6-dinitroaniline, known generally as trifluralin.

4 Claims, No Drawings

WOODY STEMMED PLANT GROWTH STIMULATION

This invention relates to plant growth regulation, particularly rose growth stimulation, and is a continuation-in-part of my copending application Ser. No. 526,819 filed Nov. 25, 1974 now U.S. Pat. No. 3,967,953 which is a continuation-in-part of my application Ser. No. 186,508, filed Oct. 4, 1971, now U.S. Pat. No. 3,861,901 which is, in turn, a continuation-in-part of my parent application Ser. No. 815,493, filed Apr. 11, 1969, now U.S. Pat. No. 3,697,253. Said parent U.S. Pat. No. 3,697,253 discloses that the herbicide N,N-di-n-propyl-4-trifluoromethyl-2,6-dinitroaniline, known generally as trifluralin, stimulated the growth of herbaceous and woody stemmed plants and increased crop yield when applied thereto in concentrations and amounts sufficient to effect growth stimulation. Said patent also discloses plant growth stimulation when trifluralin is combined with cacodylic acid and/or 2,4-dichlorophenoxyacetic acid (2,4-D) and/or 2,4,5-trichlorophenoxyacetic acid (2,4,5-T).

Said intermediate U.S. Pat. No. 3,861,901 discloses that the growth of peppers and Douglas Firs are stimulated by applying thereto trifluralin or a chlorinated phenoxyacetic acid and that the growth of soybean and alfalfa plants are stimulated by applying thereto trifluralin and 2,4-dichlorophenoxyethyl sulfate in concentrations and amounts sufficient to effect growth stimulation. Said application Ser. No. 526,819 now U.S. Pat. No. 3,967,953 discloses that the growth of roses, particularly in greenhouses, is stimulated by the application thereto of a combination of trifluralin and 2,4-D or a salt thereof or trifluralin and cacodylic acid or a salt thereof in combined concentrations and amounts sufficient to stimulate the growth of the roses.

The instant invention is based on the discovery that the normally herbicidal compound, S-ethyl-N,N-dipropylthiocarbamate, alone or in combination with trifluralin, will stimulate and increase the growth of woody stemmed plants by the application thereto of the compound or compounds in concentrations and amounts sufficient to stimulate the growth of the plants.

The invention is also based on the discovery that the growth of roses as well as their shrubs is stimulated by the application to the shrubs or bushes of compositions containing trifluralin, with or without 2,4-D and 2(2,4,5-trichlorophenoxy) propionic acid or S-ethyl-N,N-dipropylthiocarbamate, in concentrations and amounts sufficient to stimulate the growth of the roses.

Thus, the primary object of the invention is to provide methods and compositions of stimulating growth of woody stemmed plants in general and roses in particular.

The various compositions of the instant invention will be set forth hereinafter. In the data ensuing:

Compound A = N,N-di-n-4-trifluoromethyl-2,6-dinitroaniline, generically known and hereafter referred to as trifluralin.
Compound B = 2,4-dichlorophenoxyacetic acid, commonly known as 2,4-D.
Compound D = 2(2,4,5-trichlorophenoxy) propionic acid.
Compound H = S-ethyl-N,N-dipropylthiocarbamate.

Concentrates of the above compounds were made up with water, butanol and Tween #20 (polyoxyethylene sorbitan monooleate) in accordance with the following Table A, Eptam 6-E a product of Stauffer Chemical Company, New York, N. Y. containing 76.9% of S-ethyl-N,N-di-propylthiocarbamate, remainder inert ingredients, being the source of compound H. The herbicidal compound S-ethyl-N,N-di-propylthiocarbamate is disclosed in U.S. Pat. No. 2,913,327.

TABLE A

| Cmpd. | Pure Cmpd. Wt. Gm. | Tween #20 Gm. Wt. | Water Gm. Wt. | Butanol Gm. Wt. | Ml | Conc. of Cmpd. Mg/Ml | Mg/Kg (ppm) |
|---|---|---|---|---|---|---|---|
| A | 1.0407 | 102.06 | 102.06 | 51.03 | 250 | 4.163 | 4041.6 |
| B | 1.7034 | 104.28 | 104.28 | 52.14 | 250 | 6.814 | 6489.1 |
| D | 0.8517 | 108.7 | 108.7 | 54.33 | 250 | 3.407 | 3125.5 |
| H | 1.8927 | 209.02 | 209.02 | 104.5 | 500 | 3.785 | 37605.1 |

10 ml of the above concentrates diluted in 1 gallon of water provide 11 ppm compound A, 18 ppm compound B, 9 ppm compound D and 10 ppm compound H.

The concentrates were diluted in 1 gallon of tap water to provide three different strengths of spray solutions as follows:

| | |
|---|---|
| 1.1 | 10 ml A = 11 ppm |
| | 5 ml B = 9 ppm |
| 1.2 | 20 ml A = 22 ppm |
| | 10 ml B = 18 ppm |
| 1.3 | 40 ml A = 44 ppm |
| | 20 ml B = 36 ppm |
| 3.1 | 10 ml A = 11 ppm |
| | 5 ml D = 4.5 ppm |
| 3.2 | 20 ml A = 22 ppm |
| | 10 ml D = 9 ppm |
| 3.3 | 40 ml A = 44 ppm |
| | 20 ml D = 18 ppm |
| 4.1 | 10 ml A = 11 ppm |
| 4.2 | 20 ml A = 22 ppm |
| 4.3 | 40 ml A = 44 ppm |
| 5.1 | 5 ml H = 5 ppm |
| 5.2 | 10 ml H = 10 ppm |
| 5.3 | 20 ml H = 20 ppm |
| 6.1 | 10 ml A = 11 ppm |
| | 5 ml H = 5 ppm |
| 6.2 | 20 ml A = 22 ppm |
| | 10 ml H = 10 ppm |
| 6.3 | 40 ml A = 44 ppm |
| | 20 ml H = 20 ppm |

Two species, Gypsy and Fashion, of healthy undamaged rose bushes were selected for treatment in a bush nursery, each treatment group comprising 5 bushes and 2 replications, the labels marking them being distributed randomly; hence, the groups were treated in random sequence. Only after the plants were identified for treatment and labeled were the spray solutions prepared.

The spray solutions were mixed thoroughly, adjusted to an acid pH with con. HCl and kept in separate labeled bottles each equipped with a labeled spray head to avoid contamination of one spray solution with another. The sprays were applied once to the foliage and stems of the plants to drip-off. Contamination was further avoided by the fact that the treated plants were in long rows, with buffer groups in the rows between both treated and control groups, thus eliminating lineal contamination; and, further, lateral contamination was eliminated because the two species of rose bushes treated were approximately 40 feet apart, the intervening space containing about 15 rows of other species of roses, and, whenever more than a very mild air movement occurred, spraying was suspended.

The results obtained appear in the following Tables 1-3.

TABLE 1

Mean Average Number of Buds And Flowers Per Plant At The End Of The Fifth Week After Treatment (Calculated By Averaging The Count For Each Treatment Group, 2 Replications) On Field Grown Gypsy Rose Bushes. Mean Averages Of The Treatment Groups Are Given In Absolute And Indexed Form

| Treatment Groups | No. of Buds and Flowers - Mean Average | Mean Average Indexed to Control |
|---|---|---|
| 1.1 | 11.0 | 1.11 |
| 1.2 | 11.3 | 1.14 |
| 1.3 | 13.1 | 1.32 |
| 3.1 | 13.2 | 1.33 |
| 3.2 | 11.7 | 1.18 |
| 3.3 | 7.1 | .72 |
| 4.1 | 13.2 | 1.33 |
| 4.2 | 12.0 | 1.21 |
| 4.3 | 11.8 | 1.19 |
| 5.1 | 11.4 | 1.15 |
| 5.2 | 11.8 | 1.19 |
| 5.3 | 11.6 | 1.17 |
| 6.1 | 10.9 | 1.10 |
| 6.2 | 11.8 | 1.19 |
| 6.3 | 13.2 | 1.33 |
| Control | 9.92 | 1.00 |

Table 2

Mean Average Number Of Buds And Flowers Per Plant At the End Of The Fifth Week After Treatment (Calculated By Averaging The Count For Each Treatment Group, 2 Replications) On Field Grown Fashion Rose Bushes. Mean Averages Of The Treatment Groups Are Given In Absolute And Indexed Form

| Treatment Groups | No. of Buds and Flowers - Mean Average | Mean Average Indexed to Control |
|---|---|---|
| 1.1 | 35.6 | 1.05 |
| 1.2 | 39.8 | 1.18 |
| 1.3 | 33.9 | 1.00 |
| 3.1 | 39.4 | 1.17 |
| 3.2 | 34.7 | 1.03 |
| 3.3 | 34.0 | 1.01 |
| 4.1 | 37.4 | 1.11 |
| 4.2 | 36.9 | 1.09 |
| 4.3 | 40.1 | 1.19 |
| 5.1 | 27.5 | .81 |
| 5.2 | 24.3 | .72 |
| 5.3 | 33.6 | .99 |
| 6.1 | 35.3 | 1.04 |
| 6.2 | 41.5 | 1.28 |
| 6.3 | 44.8 | 1.33 |
| Control | 33.75 | 1.00 |

The data of Table 1 illustrates the effect of the various treatments upon the budding and flowering activity of the Gypsy rose bushes. The count of buds and flowers was taken for each bush in each replication, and the average number per bush for each treatment group was determined. The mean average for each treatment in both replications was then determined. Thus, the mean average data for treatment 1.1 in Table 1 is the mean average of buds and flowers per plant for the Gypsy species, calculated by adding the plant average number in each of two replications, and dividing by 2. These mean averages were then indexed to the mean average of five control groups in each replication. Five control groups were used to insure a reliable control.

Examination of Table 1 shows that in every instance except for 3.3 (44 ppm Cmpd. A plus 18 ppm Cmpd. D) the treated bushes produced from 10 to 33% more buds and flowers than did the control groups. Most notable are those above a 20% excess over control. With regard to particular treatments, it is instructive to note the positive relation between strength of treatment and excess over control in treatments 1 (Cmpd. A plus Cmpd. B) and 6 (Cmpd. A plus Cmpd. H), and the inverse relation in treatments 3 (Cmpd. A plus Cmpd. D) and 4 (Cmpd. A only). Thus, solutions stronger than 1.3 and 6.3 may well be even more productive than they, and solutions weaker than 3.1 and 4.1 may be even more productive than they are.

The data of Table 1 clearly indicates that compound H itself, namely S-ethyl-N,N-dipropylthiocarbamate, at the 5, 10 and 20 ppm levels stimulates the growth of the buds and flowers of and is tolerated by Gypsy rose plants.

Table 2 presents the same kind of data for the rose species, Fashion. This species did not respond as well to the treatments as did Gypsy; only treatments 6.2 (22 ppm A plus 10 ppm H) and 6.3 (44 ppm A and 20 ppm H) gave gains of 25% or better in buds and flowers over the control bushes.

Note the synergistic effect of mixtures of compound A, trifluralin, and compound H, S-ethyl-N,N-dipropylthiocarbamate. The sum of the percentages of buds and flowers over the control generated by compound A and compound H individually in treatments 4.2 (22 ppm H) and 4.3 (44 ppm H) and in treatments 5.2 (10 ppm H) and 5.3 (20 ppm H) as compared to the combined effect in treatments 6.2 and 6.3 shows a marked superiority of the combination of compounds A and H over the sum of the individual compound effects. This synergistic effect is most marked in the moderate strength, where the additive individual effects (4.2 + 5.2 in Table 2) yield a negative 19% (−19%) but the combination (6.2 in Table 2) yields a positive 28% (+28%) over control performance.

In addition to observing the effect of the compositions on the growth of buds and flowers, the growth of the succulent canes was also observed, the results of which appear in the following Table.

TABLE 3

$3^A$ - Total Succulent Canes Per Selected Treatment Group At 18" Above Ground Level
$3^B$ - Total Canes And Branches Per Selected Treatment Group At 18" Above Ground Level. Counts Are Given In Absolute And Indexed Form

| Treatment Groups | $3^A$ Total | Index | $3^B$ Total | Index |
|---|---|---|---|---|
| 1st Replic. | | | | |
| 1.3 | 2 | .67 | 9 | 1.29 |
| 3.1 | 2 | .67 | 9 | 1.29 |
| 4.2 | 0 | 0 | 8 | 1.14 |
| 5.1 | 2 | .67 | 7 | 1.00 |
| 5.2 | 3 | 1.00 | 9 | 1.29 |
| 2nd Replic. | | | | |
| 1.2 | 7 | 2.33 | 12 | 1.71 |
| 3.1 | 1 | .33 | 9 | 1.29 |
| 3.2 | 3 | 1.00 | 11 | 1.57 |
| 3.3 | 2 | .67 | 6 | .86 |
| 5.1 | 1 | .33 | 4 | .57 |
| 5.2 | 6 | 2.00 | 6 | .86 |
| 6.3 | 10 | 3.33 | 3 | .43 |
| Control | 3 | 1.00 | 7 | 1.00 |

Column $3^A$ of Table 3 presents findings as to succulent canes, of selected treatment groups, at 18 inches above ground level. The reasons for making this observation are as follows. First, the bushes are mowed at 18 inches for harvesting, packaging and sale. Second, succulence at that height indicates recent growth generated after treatment for new growth tends to pass the succulent condition at 7 to 10 weeks after initiation. Succulence is recognized by a reddish cast on the new growth, which reddish cast fades to green as the succulent stage is passed. Accordingly, only those canes which possessed that reddish color for at least 4 inches below the mowed height of 18 inches were counted for use in column $3^A$. Further, only those plants which had been designated as above average (on a scale of 1 to 10, 5 being average) based on determinations made in the seventh week after treatment were finally observed in the 12th week. Since the Fashion species had been mowed and harvested in that latter week, only the Gypsy species were observed. The total for control is the average of the number of succulent canes for four control groups of five plants each, while the spray group figures represent succulent canes for selected spray groups of five plants each in each replication.

Keeping in mind that the counts represented in column $3^A$ are counts of only succulent canes, not all canes, any excess over control indicates sustained vigorous growth over and above that experienced by the controls. Therefore the following treatments caused sustained vigorous growth in excess of that exhibited by the control plants: 1st Replication, none; second Replication, treatments 1.2 (22 ppm A plus 18 ppm B), 5.2 (10 ppm H) and 6.3 (40 ppm A plus 10 ppm H).

The lack of corresponding observation in the first replication does not invalidate those of the second. Thus, for example, the seventh week observation of treatment group 1.2 of the first replication showed those plants to be small, but with new, young growth. Thus, even though they were not observed in the 12th week, they did experience sustained vigorous growth, and none of the control plants were evaluated in the seventh week as having new or young growth.

Further, in the cases of treatment groups 5.2 and 6.3, the evaluations note, for those groups in the first replication, respectively, a rating of 6 (better than control) and 5 (equal to control). Accordingly, any mean total of both the latter groups would still exceed the control mean total in succulent canes, and treatment group 1.2 did show young new growth, on small plants.

It is important to note that a cane is defined as a shoot originating at five or less inches above the point at which the root stem emerges from the soil. Any shoots originating above that point are considered to be branches. Column $3^B$ is of special value, for it shows the group total of both succulent and non-succulent canes and branches at the 18 inches height (mowing height). Their significance is that when in excess of the control count, they indicate both a greater degree and longer period of growth activity than that exhibited by the controls, and a more prolific branching, therefore a more prolific crown in the rose shrub or bush.

Three treatments in both the first replication (1.3, 3.1, and 5.2) and in the second (1.2, 3.1, and 3.2) are notable. In both replications, treatment 3.1 produced 29% more succulent canes and branches at 18 inches than did the control bushes.

The superiority of the 1.3 plants in the first replication, matched to the evaluation of the same treatment group in the second, is diminished but not invalidated, for the seventh week evaluation rated the plants in the second replication as average (= to control) noting that the plants varied in state of development and that some were in tight bud. The same may be said about treatment 5.2, for the seventh week evaluation rated the 5.2 plants of the second replication at 6, slightly above average (control) condition, and noted that they were good, sturdy canes.

Treatment 1.2 in the first replication refers to plants evaluated as small, new growth and young, and so gives credence to the power of the 1.2 treatment in the second replication, which indicates a 71% excess, of all canes and branches at 18 inches, over the control performance in the 12th week.

Finally, treatment 3.2 in the second replication (57% more than control) may be paired with the following evaluation of the corresponding plants in the first replication, rated at 5, or average, equal to control.

In every instance then, except possibly for treatment 1.2, it can be said that the 1.3, 3.1, 3.2 and 5.2 treatments generated prolific branching at least equal to and in excess of that of the control plants, both in quantity and rate of growth. It should be noted further that prolific "breaks" or branching in the crown of the shrub is desirable because it causes the canes to increase in diameter, making them sturdier than those of shrubs with less prolific "breaks" or branching in the crown.

No remarkable increases in the average number of basal canes (both succulent and those no longer succulent) were observed for any treatment group over the controls although the degree of response differed between the species Gypsy and Fashion. The same was noted with respect to plant height responses.

While preferred embodiments of the invention are described herein, skilled artisans may make variations without departing from the spirit of the invention. Thus, the water soluble salts of 2,4-D (compound B) and of 2(2,4,5-trichlorophenoxy) propionic acid (compound D), such as the sodium salts, as well as the acids themselves, may be used as the active ingredients and come within the purview of the invention.

What is claimed is:

1. A method of stimulating the growth of woody stemmed plants comprising applying to the foliage and stems thereof a composition including S-ethyl-N,N-dipropylthiocarbamate and N,N-di-n-propyl-4-trifluoromethyl-2,6-dinitroaniline as the active ingredients, the combined concentrations and amounts of both compounds being sufficient to effect growth stimulation.

2. The method of claim 1 wherein the composition is applied to the plants to drip-off, the concentration of the S-ethyl-N,N-dipropylthiocarbamate being about 5–20 ppm and that of the N,N-di-n-propyl-4-trifluoromethyl-2,6-dinitroaniline being about 11 to 44 ppm.

3. The method of claim 2 wherein the concentration of the S-ethyl-N,N-dipropylthiocarbamate is about 10–20 ppm and that of the N,N-di-n-propyl-4-trifluoromethyl-2,6-dinitroaniline is about 22 to 44 ppm.

4. The method of claim 3 wherein the woody stemmed plants are roses.

* * * * *